United States Patent
Couvillion, Jr. et al.

(10) Patent No.: US 6,916,273 B2
(45) Date of Patent: Jul. 12, 2005

(54) VIRTUAL REALITY SYSTEM LOCOMOTION INTERFACE UTILIZING A PRESSURE-SENSING MAT

(75) Inventors: Warren C. Couvillion, Jr., San Antonio, TX (US); Roger R. Lopez, San Antonio, TX (US); Jian Ling, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 181 days.

(21) Appl. No.: 10/417,188

(22) Filed: Apr. 17, 2003

(65) Prior Publication Data

US 2003/0220763 A1 Nov. 27, 2003

Related U.S. Application Data

(63) Continuation-in-part of application No. 10/045,052, filed on Jan. 15, 2002.
(60) Provisional application No. 60/306,854, filed on Jul. 23, 2001.

(51) Int. Cl.[7] .............................................. A63B 22/00
(52) U.S. Cl. .............................. 482/8; 482/51; 482/54; 482/900
(58) Field of Search ........................... 482/1–9, 51, 54, 482/900–902; 345/156, 157; 702/127, 150–153

(56) References Cited

U.S. PATENT DOCUMENTS

| | | | |
|---|---|---|---|
| 5,562,572 A | 10/1996 | Carmein | |
| 5,577,981 A | 11/1996 | Jarvik | |
| 5,846,134 A | 12/1998 | Latypov | |
| 5,864,333 A | * 1/1999 | O'Heir ........................ 345/157 |
| 5,872,438 A | 2/1999 | Roston | |
| 5,902,214 A | 5/1999 | Makikawa et al. | |
| 5,980,256 A | 11/1999 | Carmein | |
| 6,050,822 A | 4/2000 | Faughn | |
| 6,052,114 A | 4/2000 | Morifuji | |
| 6,102,832 A | 8/2000 | Tani | |
| 6,106,397 A | 8/2000 | Phillips | |
| 6,114,645 A | 9/2000 | Burgess | |
| 6,135,928 A | 10/2000 | Butterfield | |
| 6,152,854 A | 11/2000 | Carmein | |
| 6,159,100 A | 12/2000 | Smith | |
| 6,336,891 B1 | * 1/2002 | Fedrigon et al. ................ 482/8 |
| 6,743,154 B2 | * 6/2004 | Epstein ........................ 482/54 |
| 2001/0045919 A1 | 11/2001 | Ishikawa et al. | |
| 2003/0018449 A1 | 1/2003 | Couvillion, Jr. et al. | |

FOREIGN PATENT DOCUMENTS

| | | |
|---|---|---|
| EP | 09050232 | 2/1997 |
| EP | 11305907 | 11/1999 |
| GB | 234 373 A | 4/1997 |
| WO | WO 97/42620 | 11/1997 |

* cited by examiner

Primary Examiner—Glenn E. Richman
(74) Attorney, Agent, or Firm—Oliff & Berridge, PLC

(57) ABSTRACT

A virtual reality system transposes a user's position and movement in real space to virtual space. The virtual reality system includes a locomotion interface that outputs signals indicative of a user's position in real space. The locomotion interface includes a pressure-sensing mat having a base layer, a plurality of pressure sensing elements and a heating/refrigeration layer formed over the base layer, and a top layer formed over the plurality of pressure-sensing elements. The plurality of pressure sensing elements output a signal indicative of pressure applied to the top layer. A virtual reality processor uses the signals output by the locomotion interface to produce an output indicative of the user's position in the virtual space corresponding to the user's position and movement in the real space. A display uses the output from the virtual reality processor to produce an image of the virtual space.

28 Claims, 3 Drawing Sheets

VIRTUAL REALITY SYSTEM LOCOMOTION INTERFACE UTILIZING A PRESSURE-SENSING MAT

BACKGROUND OF THE INVENTION

1. Field of Invention

This invention relates to virtual reality systems that can be used to fully immerse a user in virtual space.

2. Description of Related Art

Virtual reality is a computer-generated environment in which a user is immersed. Actions of the user are translated by a computer into inputs that effect the virtual environment (VE). Virtual reality systems may stimulate naturally occurring senses, such as sight, sound, touch and movement, so that a user can navigate through a virtual environment as if in the real world.

A major challenge to virtual reality system designers is to design a virtual reality system that allows natural human locomotion. Previous virtual reality systems that allow the user to move naturally require complex and expensive equipment. Other virtual reality systems abandon the concept of natural human locomotion, using simple hardware that allow the user to navigate through the virtual environment with artificial gestures, such as flying in the virtual space in the direction the user's finger is pointing.

Known virtual reality systems include treadmill devices that track the user's movement on the treadmill. Such a device is disclosed in U.S. Pat. No. 5,562,572 to Carmein. Although these treadmill devices allow movement in the user's upright position, they do not allow movement in the user's prone position. They also cannot sense whether the user is in the standing, crawling or prone position. Further, these treadmill devices are often mechanically complicated, and are thus encumbered by the inherent lag times and momentum problems associated with moving mechanical masses.

Other known virtual reality systems allow the user to move in the prone position, but sacrifice natural motion. For example, one known device includes a simple foot-pedal interface, similar to the accelerator of an automobile. The foot-pedal allows the user to move forward or backward, depending on where the user presses the foot-pedal. In this system, the user always moves toward the center of the field of view, and the field of view is rotated if the user turns his head past a certain angle. Although this system allows a user to navigate from any posture, the user must be in constant contact with the foot-pedal to navigate. It also does not enable the user to move naturally.

SUMMARY OF THE INVENTION

In various exemplary embodiments, the virtual reality system according to one aspect of this invention includes a pressure-sensing mat that outputs signals indicative of a user's position in real space. A virtual reality processor uses the signals output by the pressure-sensing mat to produce an output indicative of the virtual space corresponding to the user's position and movement in real space. A display device uses the output from the virtual reality processor to allow the user to be fully immersed in the virtual space.

In various exemplary embodiments, the pressure sensing mat includes a base layer, a plurality of pressure sensing elements formed over the base layer, and a top layer formed over the plurality of pressure-sensing elements. The plurality of pressure sensing elements output a signal indicative of pressure applied to the top layer.

This invention provides a virtual reality system that has a simple design and that allows a user to move naturally in any direction from any posture (e.g., standing, crawling, prone). The virtual reality system according to this invention has many advantages over previous virtual reality systems. The enhanced flexibility of the various exemplary embodiments of the system according to this invention allows a user to move forward, backward, or sideways from a prone, crawling or standing position. Thus, the virtual reality system according to this invention has many applications, such as, for example, enhanced military training, realistic video game environments, and a broad range of medical and therapeutic applications.

These and other features and advantages of this invention are described in, or are apparent from, the following detailed description of various exemplary embodiments of the systems and methods according to this invention.

BRIEF DESCRIPTION OF THE DRAWINGS

Various exemplary embodiments of this invention will be described in detail, with reference to the following figures, wherein.

DETAILED DESCRIPTION OF PREFERRED EMBODIMENTS

Figure 1:
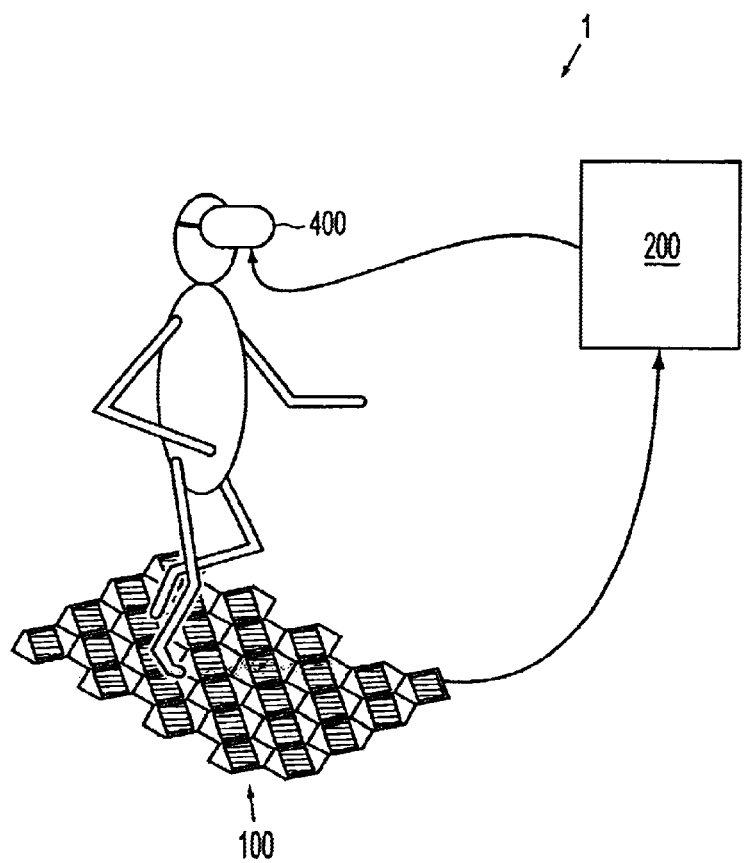
FIG. 1 illustrates one exemplary embodiment of a virtual reality system according to this invention.

FIG. 1 illustrates one exemplary embodiment of a virtual reality system according to this invention. The virtual reality system 1 includes a pressure sensing mat 100, a virtual reality (VR) processor 200, and a display 400. It should be appreciated that the various exemplary embodiments of the virtual reality system according to this invention can have any number and configuration of components that use a pressure sensing mat to sense the user's movement in order to generate a virtual environment.

Figure 2:
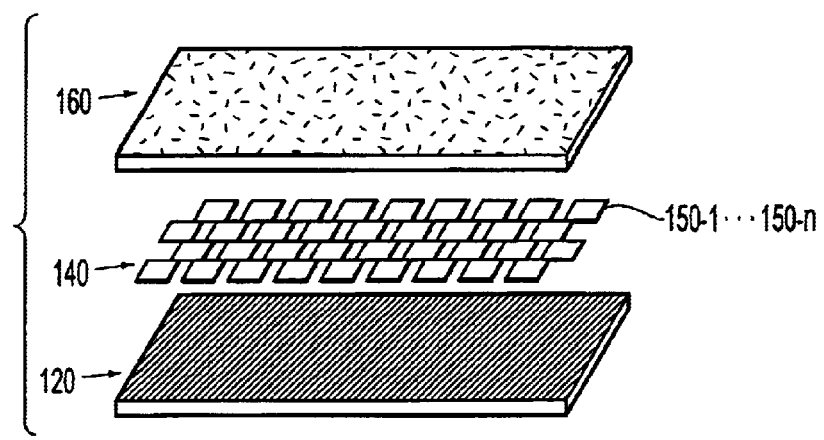
FIG. 2 illustrates one exemplary embodiment of the pressure sensing mat according to this invention.

FIG. 2 illustrates one exemplary embodiment of the pressure sensing mat 100 according to this invention. The pressure sensing mat 100 includes a semi-rigid base layer 120. Any suitable material can be used for the base layer 120, such as, for example, plastic, hardwood, and polycarbonate (lexan). A grid 140 (i.e., a two-dimensional array) of pressure sensing elements 150-1 to 150-n is formed over the base layer 120. A top layer 160 is formed over the grid 140. Any suitable layer can be used for the top layer 160, such as, for example, rubber, natural rubber, buna's rubber, and fabric reinforced negro rubber, is preferred.

The pressure sensing elements 150-1 to 150-n of the grid 140 detect the pressure applied to fixed points on the top layer 160 of the pressure sensing mat 100. Any suitable pressure sensing device can be used for the pressure sensing elements 150-1 to 150-n, such as, for example, electromechanical pressure sensors. In general, any known or later discovered pressure sensing device can be used for the pressure sensing elements 150-1 to 150-n.

Figure 3:
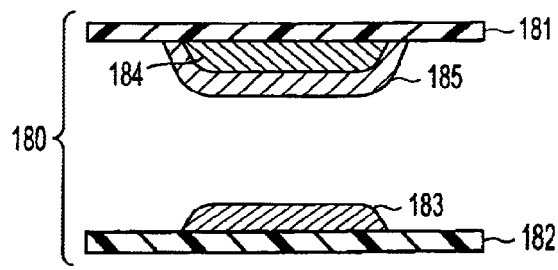
FIG. 3 shows one exemplary embodiment of a pressure sensitive resistor usable with the various exemplary embodiments of the virtual reality system according to this invention.

In the exemplary embodiment shown in FIG. 1, the pressure sensing elements 150-1 to 150-n include force sensitive resistors. As is known in the art, force sensitive resistors include elements that act as simple voltage dividers. FIG. 3 shows one exemplary embodiment of a pressure sensitive resistor 180 usable with the various exemplary embodiments of the virtual reality system according to this invention. The pressure sensing elements 150-1 to 150-n include corresponding pressure sensitive resistors 180-1 to 180-n. Each pressure sensitive resistor 180 includes an upper film 181, a lower film 182, a first electrode pattern 183 formed over the lower film 182, a second electrode pattern 184 formed over the upper film 181 so as to oppose the electrode pattern 183, and a pressure-sensitive conductor 185 formed over the second electrode pattern 184. When the upper film 181 is pressed, the pressure sensitive conductor 185 is compressed between the first and second electrode patterns. As is known in the art, the resistance of the pressure sensitive conductor 185 is lowered when compressed. Accordingly, voltage output of the pressure sensitive resistor 180 will vary with applied pressure. For more details of a pressure-sensitive resistor, see U.S. Pat. No. 5,948,990, the disclosure of which is incorporated herein by reference.

Figure 4:
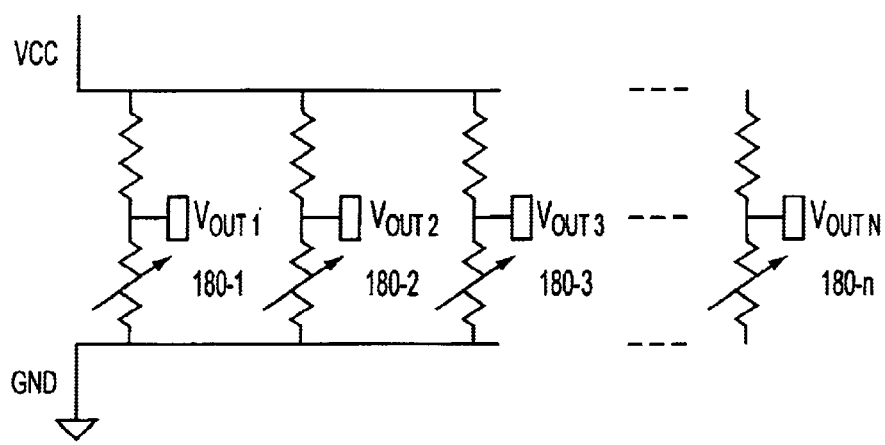
FIG. 4 illustrates the equivalent circuit of the pressure sensing mat according to this invention.

FIG. 4 illustrates the equivalent circuit of the pressure sensing mat 100. The voltage outputs Vout-1 to Vout-n correspond to respective pressure sensing elements 150-1 to 150-n that make up the grid 140. A user applies pressure to points on the pressure sensing mat 100 as the user navigates through the virtual reality environment. The applied pressures alter the resistance of the pressure sensitive resistors 180-1 to 180-n, and thus the voltage output of each of the corresponding pressure sensing elements 150-1 to 150-n varies as the user moves. The grid 140 produces a voltage output that can be analyzed to generate a pattern that shadows the user's movements in the virtual space.

Figure 5:
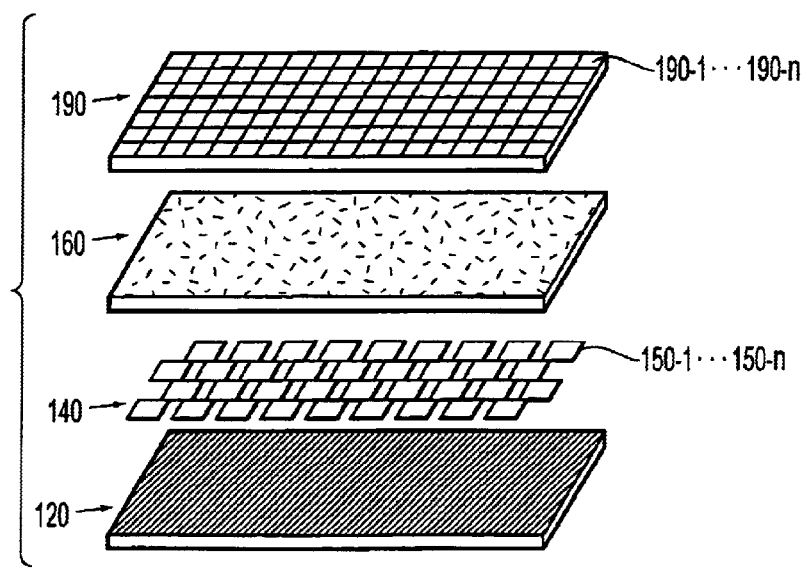
FIG. 5 shows another exemplary embodiment of the pressure sensing mat according to this invention.

FIG. 5 illustrates another exemplary embodiment of the pressure sensing mat 100 according to this invention. In this embodiment, the pressure sensing mat 100 includes the same elements as in the first embodiment, i.e., a semi-rigid base layer 120, a grid 140 of pressure sensing elements 150-1 to 150-n, and a top layer 160, and also includes a heating/refrigeration layer 190. Although FIG. 5 shows the heating/refrigeration layer 190 disposed on the top layer 160, it should be appreciated that the heating/refrigeration layer 190 can be disposed between any two layers of the pressure sensing mat 100. The heating/refrigeration units can be made up of a grid of heating/refrigeration elements 195-1 to 195-n. The heating/refrigeration elements 195-1 to 195-n can have various shapes, such that of trees, rocks and/or blades of grass, and can be formed to be rigid or flexible. Any suitable heating/refrigeration device can be used for the heating/refrigeration elements 195-1 to 195-n, such as, for example, thermoelectric devices.

In operation, the voltage output of each of the pressure sensing elements 150-1 to 150-n can be used to activate a corresponding one or group of heating/refrigeration elements 195-1 to 195-n. The heating/refrigeration elements 195-1 to 195-n can provide heat and/or cold to the user's body and surroundings as the user moves over the pressure sensing mat 100. As will be discussed in further detail, heat and/or cold generated by the heating/refrigeration elements 195-1 to 195-n can vary based on the type of virtual environment, including the virtual ground surface, generated by the virtual reality system 1.

Figure 6:
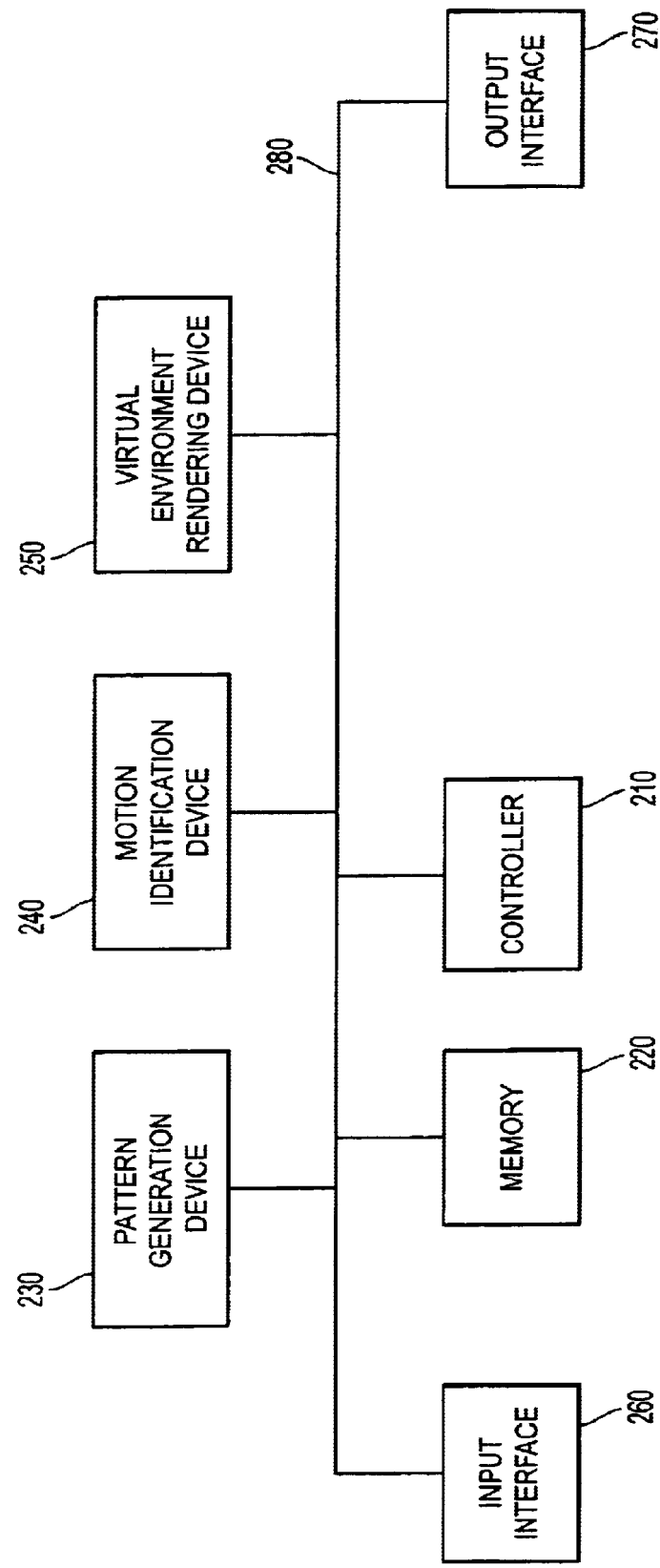
FIG. 6 is a block diagram of an exemplary embodiment of the virtual reality processor according to this invention.

FIG. 6 is a block diagram of an exemplary embodiment of the virtual reality processor 200. The virtual reality processor includes a controller 210, a memory 220 (including RAM and ROM, for example), a pattern generation device 230, a motion identification device 240, a virtual environment rendering device 250, an input interface 260, and an output interface 270. The controller 210 interfaces with the other components 220-270 using a control/data bus 280. Although the exemplary virtual reality processor 200 uses a bussed architecture, it should be appreciated that the exemplary virtual reality processor 200 can use any known or later developed architectures, including ASIC, a programmed general purpose computer, discrete logic devices, etc.

Under control of the controller 210, the input interface 260 can receive analog voltage signals from the pressure sensing elements 150-1 to 150-n. The input interface 260 can include an analog to digital converter that converts the analog voltage signals to digital signals. The input interface 260 can input the digital signals to the memory 220 for storage.

Next, the controller 210 can provide the digital signals stored in the memory 220 to the pattern generation device 230. The pattern generation device 230 samples the digital signals stored in the memory 220 at regular intervals and generates a pattern based on the digital signals at the regular intervals. The patterns generated by the pattern generation device 230 represent various positions of the user on the pressure sensing mat 100.

The controller 210 transfers the patterns generated by the pattern generation device 230 to the motion identification device 240. The motion identification device 240 can include a pattern recognition device (not shown) that identifies a given pattern with a corresponding position of the user. The pattern recognition device can identify a pattern by comparing the pattern with a database of patterns stored in the memory 220. The pattern recognition device can also recognize the pattern based on the size, shape and/or pressure distribution of the pattern. For example, if the pattern is larger than a predetermined threshold size, the pattern recognition device will recognize the pattern as a "prone user position" pattern. Similarly, if the mat outputs signals indicative of two patterns of a similar size that alternately move, the processor determines that the user is upright (e.g., walking, running or standing (if the two patterns do not move)). If more than two smaller moving patterns are detected, the user is determined to be crawling. The patterns stored in the memory 220 can provide examples for a neural network to learn how to identify different patterns.

Based on the posture and directional information determined by the processor, the virtual environment (i.e., the displaying image) is appropriately altered.

A series of user positions identified by the pattern recognition device can be stored in the memory 220 during fixed intervals as the user navigates through the virtual environment. Preferably, the centroid of each of the patterns in the series of patterns is tracked as the user moves on the pressure sensing mat 100. The motion identification device 240 can sample the series of user positions at the end of the fixed intervals and identify the motion of the user during the fixed intervals based on the series of user positions. The motion includes, for example, direction (forward, backward, left, right, etc.) and speed. The patterns also can be analyzed to determine the posture (standing, crawling, prone) of the user.

The direction that the user is facing is determined by a sensor that can be directly attached to the user. In embodiments, the sensor can be a magnetic tracker attached to the user's waist that determines the direction the waist is facing. The virtual reality system according to this invention provides significant advantages over known virtual reality systems in that only a single sensor needs to be directly attached to the user. Thus, the user is relatively free from cumbersome sensor wiring and devices.

The controller 210 can transpose the motion of the user into the virtual environment generated by the virtual environment rendering device 250. Data for the virtual environment, including virtual objects, can be stored in the memory 220. The virtual environment rendering device 250 can update the virtual environment at given intervals based on the data stored in the memory 220. The virtual environment rendering device 250 can update the virtual space each time the user's motion is identified. Thus, as the user moves through the virtual space, the user can effect, and can be effected by, the virtual environment. For example, as the user navigates through the virtual space, the user's perspective in the virtual space can change, virtual objects can enter the user's path, and the user can move virtual objects.

The virtual environment rendering device 250 can also generate a virtual ground surface, depending on the user's location in the virtual space. The type of virtual ground surface generated by the virtual environment rendering device 250 can determine the amount of heat and/or cold air generated by the heating/refrigeration layer 190 of the pressure sensing mat 100. For example, if the virtual ground surface is ice, the heating/refrigeration layer 190 can be controlled to generate cold air under the user's body. As discussed above, the heating/refrigeration elements 190-1-190-n that make up the heating/refrigeration layer 190 can have various shapes that protrude from the pressure sensing mat 100, so that various types of objects, such as frozen trees, hot desert rocks, etc., can be more realistically simulated in the virtual environment. The heating/refrigeration elements 190-1-190-n can also be removable from the pressure sensing mat 100 so that they can be replaced with heating/refrigeration elements 190-1-190-n of different shapes and sizes, depending on the virtual environment to be simulated.

The controller 210 can control the output interface 270 to output virtual reality environment data to the display 400. Although the display 400 is shown in FIG. 1 as a head-mounted display, any known or later discovered display can be used. Preferably, the display provides the user with the ability to see, hear, smell and/or touch in the virtual world so that the user is fully immersed in the virtual space.

In embodiments, it is conceivable that the pressure sensing mat 100 can be as large as required to allow the user to move as if the user was in the virtual space. For example, the pressure sensing mat 100 can be made to cover the floor of a large field or room. Alternatively, if space is limited, the pressure sensing mat 100 can be made smaller, in which case the user would be required to move in a bounded area or move "in place".

The virtual reality system 1 can be implemented as software executing on a programmed general purpose computer, a special purpose computer, a microprocessor or the like.

While the invention has been described with reference to exemplary embodiments thereof, it is to be understood that the invention is not limited to the preferred, exemplary embodiments or constructions. To the contrary, the invention is intended to cover various modifications and equivalent arrangements. In addition, while the various elements of the exemplary embodiments are shown in various combinations and configurations, which are exemplary, other combinations and configurations, including more, less or only a single element, are also within the spirit and scope of the invention.

What is claimed is:

1. A locomotion interface that provides input signals, indicative of a user's movement, to a virtual reality system, the locomotion interface comprising:
a pressure-sensing mat including a base layer, a plurality of pressure sensing elements and a heating/refrigeration layer formed over the base layer, and a top layer formed over the plurality of pressure-sensing elements, wherein the plurality of pressure sensing elements output signals indicative of pressure applied to the top layer.

2. The locomotion interface of claims 1, wherein the heating/refrigeration layer is made up of a plurality of heating/refrigeration elements.

3. The locomotion interface of claim 2, wherein the plurality of heating/refrigeration elements make up a grid.

4. The locomotion interface of claim 2, wherein the heating/refrigeration elements are thermoelectric devices.

5. The locomotion interface of claim 1, wherein the plurality of pressure-sensing elements make up a grid.

6. The locomotion interface of claim 1, wherein the plurality of pressure-sensing elements comprise force sensitive resistors.

7. The locomotion interface of claim 1, wherein the base layer comprises a semi-rigid material.

8. The locomotion interface of claim 1, wherein the base layer comprises plastic.

9. The locomotion interface of claim 1, wherein the top layer comprises rubber.

10. A virtual reality system comprising the locomotion interface of claim 1.

11. A virtual reality system that transposes a user's position and movement in real space to virtual space, the virtual reality system comprising:
a locomotion interface that outputs signals indicative of a user's position in real space, the locomotion interface including a pressure-sensing mat including a base layer, a plurality of pressure sensing elements and a heating/refrigeration layer formed over the base layer, and a top layer formed over the plurality of pressure-sensing elements, the plurality of pressure sensing elements output signals indicative of pressure applied to the top layer;
a virtual reality processor that uses the signals output by the locomotion interface to produce an output indicative of the user's position in the virtual space corresponding to the user's position and movement in the real space; and
a display that uses the output from the virtual reality processor to produce an image of the virtual space.

12. The locomotion interface of claims 11, wherein the heating/refrigeration layer is made up of a plurality of heating/refrigeration elements.

13. The locomotion interface of claim 12, wherein the plurality of heating/refrigeration elements make up a grid.

14. The locomotion interface of claim 12, wherein the heating/refrigeration elements are thermoelectric devices.

15. The virtual reality system of claim 11, wherein the display is a head mounted display.

16. The virtual reality system of claim 11, wherein the plurality of pressure-sensing elements make up a grid.

17. The virtual reality system of claim 11, wherein the plurality of pressure-sensing elements comprise force sensitive resistors.

18. The virtual reality system of claim 11, wherein the base layer comprises a semi-rigid material.

19. The virtual reality system of claim 11, wherein the base layer comprises plastic.

20. The virtual reality system of claim 11, wherein the top layer comprises rubber.

21. The virtual reality system of claim 11, wherein the virtual reality processor comprises:

a pattern generator that uses the signals output from the locomotion interface to generate a plurality of corresponding patterns;

a motion identifier that uses the plurality of patterns generated by the pattern generator to identify a corresponding plurality of user positions and user movements; and a virtual environment renderer that uses the identified user positions and movements to generate a virtual space such that the user can effect, and be effected by, the virtual space.

22. The virtual reality system of claim 21, wherein the virtual space generated by the virtual environment renderer includes a virtual ground surface.

23. The virtual reality system of claim 22, wherein the virtual ground surface generated by the virtual environment renderer determines the amount heat and/or cold generated by the heating/refrigeration layer.

24. The virtual reality system of claim 21, wherein the plurality of positions identified by the motion identifier comprise at least one of a prone user position, a crawling user position, and a standing user position.

25. The virtual reality system of claim 21, wherein the plurality of motions identified by the motion identifier comprise at least one of a backward user motion, a sideways user motion, a forward user motion, and a diagonal user motion.

26. A method of providing input signals, indicative of a user's movement, to a virtual reality system, comprising:

sensing pressure applied to a locomotion interface having a pressure-sensing mat including a base layer, a plurality of pressure sensing elements and a heating/refrigeration layer formed over the base layer, and a top layer formed over the plurality of pressure-sensing elements.

27. The method of claim 26, further comprising:

processing signals output by the locomotion interface, in response to the sensed pressure, to produce an input signal indicative of the user's position in virtual space corresponding to the user's position and movement in real space.

28. The method of claim 26, wherein the step of processing the signals output by the locomotion interface comprises:

generating a plurality of patterns that correspond to the signals output by the locomotion interface; and identifying a plurality of user positions and user movements that correspond to the plurality of patterns.

* * * * *

UNITED STATES PATENT AND TRADEMARK OFFICE
CERTIFICATE OF CORRECTION

PATENT NO. : 6,916,273 B2
APPLICATION NO. : 10/417188
DATED : July 12, 2005
INVENTOR(S) : Couvillion, Jr. et al.

It is certified that error appears in the above-identified patent and that said Letters Patent is hereby corrected as shown below:

On the Title Page, item (56), under "FOREIGN PATENT DOCUMENTS", in Column 2, Line 1, delete "EP 09050232 2/1997" and insert -- JP JP09050232 2/1997 --, therefor.

On the Title Page, item (56), under "FOREIGN PATENT DOCUMENTS", in Column 2, Line 2, delete "EP 11305907 11/1999" and insert -- JP JP11305907 11/1999 --, therefor.

In Column 1, Line 5, Heading
insert -- CROSS-REFERENCE TO RELATED APPLICATIONS --.

In Column 1, Line 6, insert -- This application is a Continuation-in-Part of Application No. 10/045,052 filed January 15, 2002, which in turn is a Non-Provisional application of U.S. Provisional Application No. 60/306,854 filed July 23, 2001. The entire disclosure of the prior applications is hereby incorporated by reference herein in its entirety. --.

In Column 6, Line 15, in Claim 2, delete "claims" and insert -- claim --, therefor.

In Column 6, Line 54, in Claim 12, delete "claims" and insert -- claim --, therefor.

In Column 7, Line 26, in Claim 23, delete "amount heat" and insert -- amount of heat --, therefor.

Signed and Sealed this
Eighth Day of January, 2013

David J. Kappos
*Director of the United States Patent and Trademark Office*